US00PP10517P

United States Patent [19]

Lemon

[11] Patent Number: Plant 10,517

[45] Date of Patent: Jul. 21, 1998

[54] VARIETY OF GERANIUM PLANT NAMED 'PATRIOT BRIGHT PINK'

[75] Inventor: David Lemon, Lompoc, Calif.

[73] Assignee: John Bodger & Sons Company, So. El Monte, Calif.

[21] Appl. No.: 724,710

[22] Filed: Oct. 1, 1996

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Fulwider Patton Lee & Utecht, LLP

[57] ABSTRACT

The cultivar is characterized by its sharp candy pink color above medium green foliage. Its quick rooting time and continuous flowering provides for superb cuttings and for quick recovery of the bloom following wet weather conditions. The cultivar performs well either indoors or out of doors, and an abundant amount of cuttings may be obtained from a single plant.

2 Drawing Sheets

BACKGROUND OF THE NEW PLANT

The present invention comprises a new and distinct cultivar of *Pelargonium×hortorum* known by the varietal name Patriot Bright Pink (Oglevee No. 3051, Bodger No. 2GM 226-1). The new variety was discovered in a selective breeding program by David Lemon at Bodger Seeds, Ltd., Lompoc, Calif. The new variety is a selection from the crossing of Bodger No. 10 GM 181-4 (unpatented) which is a red seedling with Bodger No. 10 GM 148-1 (unpatented) which is a red seedling.

The new cultivar was first asexually reproduced by cuttings at Oglevee Ltd., Connellsville, Pa., and has been repetatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWINGS

The accompanying drawings illustrate the new cultivar, the colors depicted being as nearly true as possible with color illustration of this type.

Sheet 1 represents a side view of the new cultivar.

Sheet 2 is a top view.

DESCRIPTION OF THE NEW PLANT

The following detailed description sets forth characteristics of the new cultivar. The data which defines each characteristics was collected from asexual reproductions carried out by Oglevee Ltd. in Connellsville, Pa. The plant histories were taken on rooted cuttings believed to have been potted on approximately Feb. 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:
- *Botanical.*—Pelargonium×hortorum.
- *Commercial.*—Florist's Zonal Geranium Patriot Bright Pink (Florist's geraniums are a high quality plant which also grows well outdoors.

Form: Uniform, medium mound habit.
- *Height.*—16.0–18.0 cm from top of pot.
- *Growth.*—Free basal branching.
- *Strength.*—No artificial support needed.

Foliage: Stalked leaf attachment.

Leaves:
- *Size.*—8.0–9.5 cm fully expanded.
- *Shape.*—Reniform; cordate base.
- *Margin.*—Crenate.
- *Texture.*—Slightly pubescent.
- *Color.*—Top: Green group 137C. Bottom: Yellow-green group 146B. Zone: Green group 137B.
- *Ribs and veins.*—Palmate venation: Color: Yellow-green group 145B.

Petioles:
- *Length.*—8.0–9.5 cm.
- *Color.*—Yellow-green group 146B.

Stem:
- *Color.*—Yellow-green group 146D.
- *Internodes.*—3.0 cm–4.5 cm.

The Bud (Umbel)

Shape: Upright hemispherical cluster.

Size: 3.0–3.5 across; buds showing color.

INFLORESCENCE

Blooming habit: Semi-double (any floret with 6 or more petals which still have anthers and filaments); continuous blooming.

Borne: Umbel; florets on pedicel, pedicel on peduncle; 4.0–8.0 cm above foliage.

Closed florets:
- *Bud size.*—0.5–1.5 cm in length; 0.5–1.0 cm across.

Size:
- *Fully open bloom.*—10.0–11.5 cm across.

Open florets:
- *Form.*—Flat to slightly cupped; 24 florets per in florescence appearing.
- *Color.*—Upper: base coloration is red group 43D with the margin or tip red group 52C and on the inner petals the margin is 52D. Bottom: Red group 49B with a margin of red Group 52C. Eye: None.

*Petals.*—6–7 in number.

*Size.*—4.5–5.0 cm across.

*Texture and appearance.*—Satiny; appearance from a distance is a bright candy pink above medium green foliage.

Petaloids:

*Quantity.*—3–5.

*Shape.*—Elongated, twisted, some are petal-like with pollen attached (the structure may not change completely to a full petaloid form and may retain some anther characteristics).

*Color.*—Top: Red group 52D. Bottom: Red group 49B.

Pedicel:

*Length.*—2.5–3.0 cm.

*Color.*—Yellow-green group 146D.

Peduncle:

*Length.*—18.0–20.0 cm.

*Color.*—Yellow green group 146B.

Persistence:

*Disease resistance.*—Not known.

*Lasting quality.*—Garden performance is very good.

Reproductive Organs

Stamens:

*Anthers.*—Length: 2–3 mm.

*Filaments.*—Length: 6–7 mm. Color: White.

*Pollen.*—Orange-brown.

Pistils:

*Number.*—1.

*Length.*—8–9 mm.

*Stigma.*—Color: Red-purple, 5–6 parted.

*Style.*—Length: 2–3 mm.

Ovaries:

*Color.*—Pubescent; yellow-green, superior.

*Length.*—4–5 mm.

Fruit: None.

General Characteristics

Patriot Bright Pink brings a new color to geraniums, a true sharp candy pink above medium green foliage. Patriot Bright Pink exhibits very good indoor and outdoor performance. These plants root quickly averaging 12 days while the plants bloom early thus the finishing time is satisfactory. The cutting production is typically 40 or more cuttings per stock plant.

I claim:

1. A new and distinct variety of Geranium plant, substantially as shown and described.

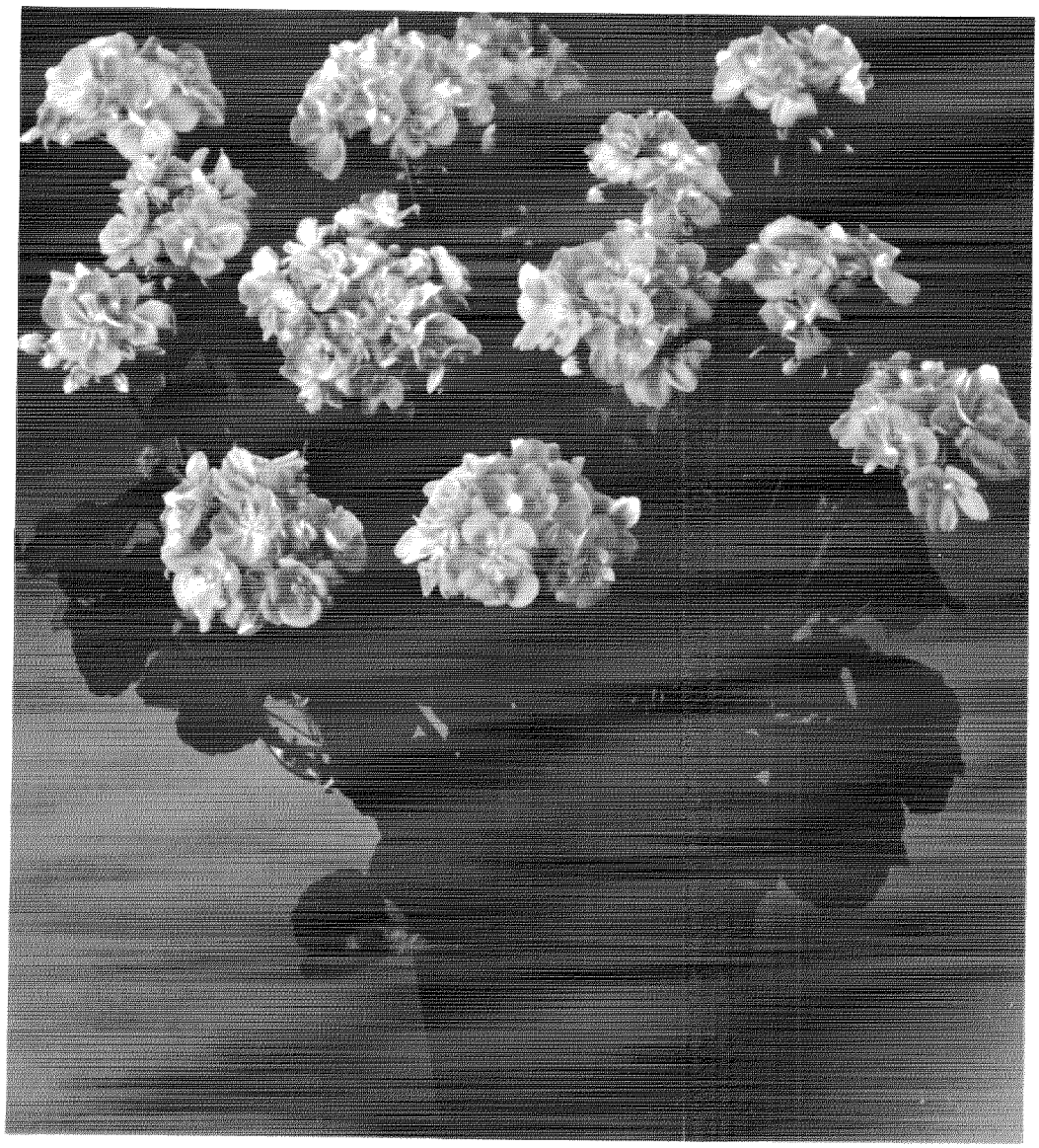

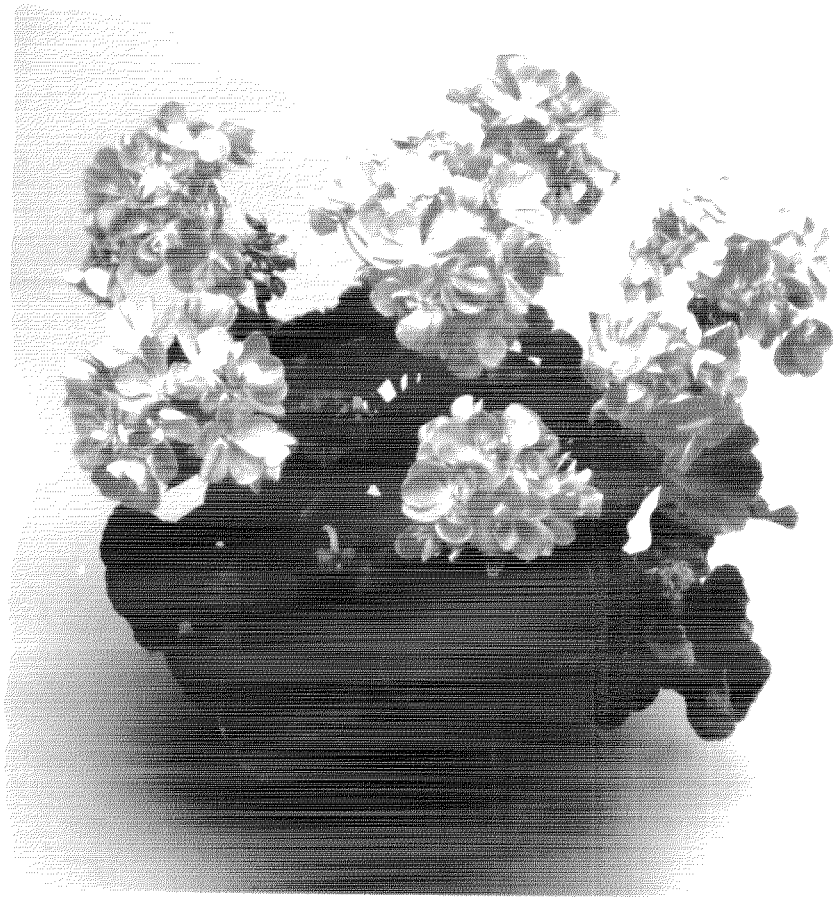

* * * * *